US006570028B1

United States Patent
Heymans et al.

(10) Patent No.: US 6,570,028 B1
(45) Date of Patent: May 27, 2003

(54) PROCESS FOR THE PREPARATION OF GLYCIDYLESTERS OF BRANCHED CARBOXYLIC ACIDS

(75) Inventors: Denis Marie Charles Heymans, Amsterdam (NL); Leo Wim Van Noort, Amsterdam (NL); Jozef Jacobus Titus Smits, Amsterdam (NL); Hendrik Stichter, Amsterdam (NL)

(73) Assignee: Resolution Performance Products LLC, Houston, TX (US)

( * ) Notice: Subject to any disclaimer, the term of this patent is extended or adjusted under 35 U.S.C. 154(b) by 0 days.

(21) Appl. No.: 09/703,158

(22) Filed: Oct. 31, 2000

(30) Foreign Application Priority Data

Feb. 25, 2000 (EP) .............................. 00200665

(51) Int. Cl.⁷ ..................... C07D 301/24; C07D 301/00
(52) U.S. Cl. ........................ 549/520; 549/540
(58) Field of Search ................. 549/540, 520

(56) References Cited

U.S. PATENT DOCUMENTS 3,644,431 A * 2/1972 Heer et al. ............... 549/540
4,981,926 A * 1/1991 Pham et al. ............. 549/540

* cited by examiner

Primary Examiner—Alan L. Rotman
Assistant Examiner—Raymond Covington
(74) Attorney, Agent, or Firm—Lisa Kimes Jones

(57) ABSTRACT

Process for the manufacture of diglycidylesters of $\alpha,\alpha'$-branched dicarboxylic acids, comprising (a) the reaction of the $\alpha,\alpha'$-branched dicarboxylic acid with a halo substituted monoepoxide such as an epihalohydrin, in a 1.1–20 acid equivalent ratio relative to the $\alpha,\alpha'$-branched aliphatic dicarboxylic acid, optionally in the presence of water and water-miscible solvent, and in the presence of a catalyst in an amount of at most 45 mol % of the acid equivalent amount of the $\alpha,\alpha'$-branched aliphatic dicarboxylic acid, at a temperature in the range of from 30 to 110° C., during a period in the range of from 0.5 to 2.5 hr, (b) addition of alkali metal hydroxide or alkali metal alkanolate up to an acid equivalent ratio as to the $\alpha,\alpha'$-branched aliphatic dicarboxylic acid in the range of from 0.9:1 to 1.2:1, and reaction at a temperature of from 0 to 80° C., (c) distillation of the obtained reaction mixture to remove the excess halo substituted monoepoxide and the solvent and water formed, and (d) removal of alkali metal halide salt, preferably by washing the obtained diglycidylester with water mixed with an inert organic solvent, after optionally treating the residual product with a concentrated aqueous alkali metal hydroxide solution, in order to complete the dehydrohalogenation.

22 Claims, No Drawings

PROCESS FOR THE PREPARATION OF GLYCIDYLESTERS OF BRANCHED CARBOXYLIC ACIDS

FIELD OF THE INVENTION

The present invention relates to a process for the preparation of glycidylesters of branched carboxylic acids.

BACKGROUND OF THE INVENTION

More in particular the present invention relates to a multistep process for the preparation of glycidylesters of $\alpha,\alpha'$-branched dicarboxylic acids.

Glycidylesters of $\alpha$-branched carboxylic acids are useful for the preparation of epoxy resins, acrylic polyester resins and alkyd resins, either directly or via intermediate products such as adducts with (meth)acrylic acid amines, polyols and polyacids, or as reactive diluents for the preparation of thermoset acrylic, epoxy, polyester and/or urethane paints and coatings.

Glycidylesters of mono, $\alpha$-branched carboxylic acids and their method of preparation are disclosed in U.S. Pat. No. 3,075,999, 3,178,454, 3,275,583 and 3,397,176.

In particular diglycidylesters of $\alpha,\alpha$-branched aliphatic dicarboxylic acids and diglycidyl esters of $\alpha,\alpha,\alpha',\alpha'$-branched aliphatic dicarboxylic acids are known from NL-286209A, DT-OL 1942836A, U.S. 3,629,295A, GB-1,360,811B, GB-1,360,812B, GB-1,360,813B, EP-0518408B1 and from WO98/52932.

In the majority of said publications, said glycidyl-esters are made by reacting an alkali salt of the carboxylic acid with a halo-substituted monoepoxide such as an epihalohydrin, e.g., epichlorohydrin (1–20 molar excess). The mixture is heated (50–150° C.) in the presence of a catalyst forming glycidylester plus alkali salt and water. The water and excess epihalohydrin are removed by azeotropic distillation, and the salt by-product, e.g., NaCl, is removed by filtration and/or washing. The glycidylesters can also be made by reacting the carboxylic acid directly with epichlorohydrin under similar process conditions. The chlorohydrin ester intermediate formed during this reaction is subsequently treated with an alkaline material, e.g., sodium or potassium hydroxide, which yields the desired glycidylester. By-product salt is removed by washing and/or filtration, and water is removed by drying.

However, said conventional processes have appeared to provide glydicylesters which showed unattractive halogen contents, making them not applicable for highly sophisticated coating applications on metal substrates, for which high corrosion resistances are required.

On the other hand the economics of modern coating industries, in which an important proportion of the total output of said glycidylesters is used as starting material, required lower prices per unity active product (i.e. higher EGC values) and related therewith lower manufacturing costs of said glycidylester starting materials.

In the more recent publication WO98/52932 diglycidylesters of a specific group of 3,4,5,6-alkyl-substituted cyclohexane-1,2-dicarboxylic acid were prepared by means of a Diels-Alder reaction of maleic anhydride and specific dienes, such as allo-ocimene.

However again, the products of such a preparation were characterized by relative low EGC values (as compared to the theoretical yield) and a relatively bad efficiency.

It will be appreciated that for particular application of said glydicylesters in clear coatings, there has been developed a growing need for colourless and colour stable products.

It is generally known that mono- and diglycidylesters are thermally and chemically reactive molecules, which cannot be easily recovered from initially prepared, coloured crude glycidylesters.

It has been found that standard atmospheric distillation techniques usually increase the amount of by-products as well as the degree of colour of the esters. It is known that this increase in colour is caused by the reaction at elevated temperatures, as encountered during distillation, of the glycidyl functionality present in the desired product with functionalities present in the by-products, thereby forming additional by-products, which are not separable from the glycidylester and which are extremely sensitive to discoloration upon heating.

It will be appreciated that there is still a need for an improved manufacturing process for glycidylesters of $\alpha,\alpha'$-branched dicarboxylic acids, and in particular of $\alpha,\alpha,\alpha',\alpha'$-branched aliphatic dicarboxylic acids, which may lead to diglycidylesters of the performance of the product aimed at, and at a lower cost price.

An object of the present invention therefor is to provide a process for the manufacture of glycidylesters of $\alpha,\alpha'$-branched dicarboxylic acids, with significantly lower halogen content (i.e. total halogen content and hydrolyzable halogen content), heat stability and colour stability and/or higher purity, which must be reached at a reduced cost price per product unit.

As a result of extensive research and experimentation, such a process has been surprisingly found now.

SUMMARY OF THE INVENTION

Accordingly, the invention relates to a process for the manufacture of diglycidylesters of $\alpha,\alpha'$-branched dicarboxylic acids, comprising (a) the reaction of the $\alpha,\alpha'$-branched dicarboxylic acid with a halo substituted monoepoxide such as an epihalohydrin (e.g. epichlorohydrin) in a 1.1–20 acid equivalent ratio relative to the $\alpha,\alpha'$-branched aliphatic dicarboxylic acid and preferably in acid equivalent ratio of 3–20, optionally in the presence of water and water-miscible solvent and preferably an aqueous alkanol as solvent, and in the presence of a catalyst in an amount of at most 45 mol % of the acid equivalent amount of the $\alpha,\alpha'$-branched aliphatic dicarboxylic acid, and preferably at most 20% and more preferably of at most 10%, at a temperature in the range of from 30 to 110 (and preferably from 65 to 95° C.), during a period in the range of from 0.5 to 2.5 hr, (b) addition of alkali metal hydroxide or alkali metal alkanolate up to an acid equivalent ratio as to the $\alpha,\alpha'$-branched aliphatic dicarboxylic acid in the range of from 0.9:1 to 1.2:1 and preferably from 0.95:1 to 1.10:1 and reaction at a temperature of from 0 to 80° C. (and preferably from 20 to 70° C.), (c) distillation of the obtained reaction mixture to remove the excess halo substituted monoepoxide and the solvent and water formed, and (d) removal of alkali metal halide salt, preferably by washing the obtained diglycidylester with water mixed with an inert organic solvent, after optionally treating the residual product with a concentrated aqueous alkali metal hydroxide solution, in order to complete the dehydrohalogenation (and preferably a dehydrochlorination).

It will be appreciated that the diglycidylester obtained after step (d), can be dried in addition e.g. by distillation or treating with water absorbers.

DETAILED DESCRIPTION OF THE INVENTION

The process according to the present invention can be carried out either as batch process or as a continuous process. The process preferably uses α,α,α',α'-branched aliphatic dicarboxylic acids, containing from 8 to 24 carbon atoms.

Of particular interest are diglycidylesters of α,α'-branched aliphatic carboxylic acids represented by the formula:

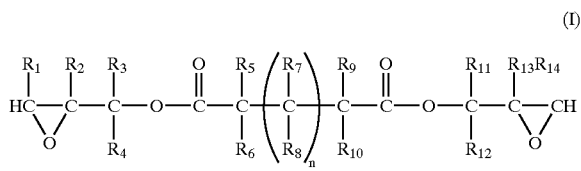

wherein $R_1$, $R_2$, $R_3$, $R_4$, $R_5$, $R_7$, $R_8$, $R_9$, $R_{11}$, $R_{12}$, $R_{13}$ and $R_{14}$ may be the same or different and each may represent hydrogen or a lower alkyl group containing from 1–4 carbon atoms and preferably 1 or 2 carbon atoms, wherein $R_6$ and $R_{10}$ may be the same or different and each may represent an alkyl group containing from 1 to 10 carbon atoms and preferably from 1 to 4 or a cycloaliphatic ring having 5 or 6 carbon atoms, optionally substituted with one or more lower alkyls, and wherein the total carbon atoms in the diacid part of the diglycidyl esters of formula 1 are in the range of from 8 to 24 carbon atoms, and preferably from 10 to 14 carbon atoms, and wherein n is an integer in the range of from 0 to 8, and preferably from 2 to 6.

Preferred diglycidylester of dicarboxylic acids of formula I are those wherein $R_5$, $R_6$, $R_9$ and $R_{10}$ are methyl and/or ethyl groups, wherein $R_7$ and $R_8$ are hydrogen, and n is in the range of from 2 to 6.

With the term "alkanol" as used throughout this specification are meant mono-alkanol as well as polyalkanols, such as glycols. More preferably as alkanol isopropyl alcohol is used.

The amount of alkanol in the aqueous alkanol solution is preferably at least one mole alkanol per mole dicarboxylic acid.

The preferred reaction time in step (a) is in the range of from 0.9 to 1.5 hours.

The catalyst to be used in step (a) may be selected from alkalimetal hydroxides, alkalimetal carbonates, alkaline earth hydroxides, alkalimetal or alkaline earth metal alcoholates of the formula $X^{n+}(OR^-)_n$, wherein X represents the alkali metal or alkaline earth metal ion and R represents $C_1$–$C_{12}$ alkyl, n represents the valence of the metal ion, or ammonium salts and in particular hydroxides or halides of the formula $R_{15}R_{16}R_{17}R_{18}N^\oplus Y^-$, wherein $R_{15}$, $R_{16}$ and $R_{17}$ independently of each other may represent an alkyl group having from 1 to 16 carbon atoms, which optionally may be substituted with one or more hydroxyl groups, wherein $R_{18}$ represents an alkyl group having from 1 to 16 carbon atoms, phenyl, benzyl, or cycloalkyl of 5 or 6 carbon atoms, and wherein Y represents hydroxyl or halogen.

Another suitable group of basic catalysts for step (a) is formed by phosphonium halides of the formula $R_{20}R_{21}R_{22}R_{23}P^\oplus Z^-$, wherein $R_{20}$, $R_{21}$, $R_{22}$ and $R_{23}$ independent of each other may represent monovalent hydrocarbon groups. Preferably $R_{20}$, $R_{21}$ and $R_{22}$ are alkyl, cycloalkyl, aryl, aralkyl, having at most 25 C-atoms and more preferably having at most 18 C-atoms, such as phenyl, butyl, octyl, lauryl, hexadecyl or cyclohexyl. $R_{23}$ is preferably an alkyl group of from 1 to 10 C-atoms and more preferably of from 1 to 4 and wherein Z is a halogen, such as chlorine, bromine or iodine.

Alkalimetal hydroxides or alkali metal alkanolates having from 1 to 6 carbon atoms are most preferred as catalyst in step (a).

The alkalimetal hydroxide which is used in step (a) may be selected from sodium hydroxide, potassium hydroxide, lithium hydroxide, rubidium hydroxide, and cesium hydroxide, of which sodium hydroxide or potassium hydroxide is more preferred. It will be appreciated that in step (b) only relatively strong and water-soluble metal hydroxides or metal alcoholates have to be used, whereas weaker, less water-soluble metal hydroxides or carbonates are less preferred.

It will be appreciated that the specified molar ratios in step (b) will be constituted by additions of alkali metal hydroxides or alkali metal alkanoates on both steps (a) and (b).

With the term "distillation" used in step (c) is meant removal of the light fractions from the initially obtained reaction mixture (which is indicated in the art as "topping").

In addition, according to a preferred embodiment of the present invention the brine formed in step (a) can be completely or partially removed before entering step (b).

The alkali metal hydroxide or alkali metal alkanolate which is used in steps (b) and (d) are preferably selected from sodium hydroxide, sodium alkanolate having from 1 to 6 carbon atoms, such as sodium isopropanolate, lithium hydroxide or lithium alcoholate. Most preferably sodium hydroxide or sodium alkanolate having from 1 to 6 carbon atoms is used.

Preferably for step (b) sodium hydroxide is used in an aqueous solution of a concentration of from 10 to 60% by weight and more preferably from 20 to 50% by weight.

It will be appreciated that according to the process of the present invention a drying cq. solvent removal step can take place after the washing in step (d), if desired.

It will be appreciated that the process of the present invention can be applied on sole α,α'-branched aliphatic dicarboxylic acids or on mixtures thereof.

Mixtures of diglycidylesters of α,α'-branched aliphatic dicarboxylic acids are produced, when starting from technical grades of commercially available compositions of α,α'-branched aliphatic dicarboxylic isomers.

Examples of such acids are 2,4-dimethylglutaric acid, 2,5,5-trimethyladipic acid, 2,2,4,4-dimethylglutaric acid, 2,2,5-trimethyladipic acid, 2,3-dimethylsuccinic acid, 2,2,3,3-tetramethylsuccinic acid, 2,2,6,6-tetra-methylpimelic acid, 2,5-dimethyladipic acid, 2,2,5-tri-methyladipic acid, 2,2,5-trimethyl-5-ethyladipic acid, 2,9-dibutylsebacic acid, 2,2,9,9-tetramethylsebacic acid, 2,2,7,7-tetramethylsuberic acid, 2,2,6-trimethyl-6-ethylpimelic acid and 2,2,5,5-tetramethyladipic acid.

Preferably di-carboxylic acids having 8 to 14 carbon atoms are used as starting material.

It will be appreciated that according to the more preferred embodiments of the process of the present invention step (d) will be carried as anhydrous as possible, i.e. using highly concentrated sodium hydroxide solutions e.g. up to 55 wt %.

It has surprisingly been found, that the process of the present invention can provide very pure glycidylesters of α,α'-branched aliphatic dicarboxylic acid, i.e. showing contents of heavier byproducts less than 6 wt % and preferably less than 5 wt. and more preferably less than 4 wt %, which show the desired reduced initial colour, the improved colour stability after extended periods of storage, which surprisingly show a low total halogen content and in particular total chlorine content (e.g. ≦1400 mg/kg) and a low hydrolyzable halogen, and in particular chlorine, contents (e.g. 450 mg/kg), and which do not need tailing by distillation for purification, while the process can be further characterized by a very high conversion and selectivity of the halo substituted epoxide with reference to the desired glycidylester. Moreover a very efficient and easy phase separation could be obtained in the last recovery step.

More in particular it could not be expected by a person skilled in the art that the presence of a base in steps (b) and (d) does not significantly hydrolize the present, just formed glycidylester.

It will be appreciated that preferably an alkanol will be used which enables the dissolution of a sufficient amount of base into the organic phase, whereas on the other hand the total water content in the reaction mixture of step (a) is to be kept in the range of from 4 to 13 mol/mol acid.

The process of the present invention is more preferably carried out, starting from α,α,α',α'-branched aliphatic dicarboxylic acids, containing from 8 to 14 carbon atoms in the acid moiety, and most preferably from 10 to 14 carbon atoms.

According to a preferred embodiment of the process of the invention, the initially prepared diglycidylester is washed in step (d) with a mixture of water and solvent which facilitates the phase separation aimed at. More preferably a weight ratio of solvent and diglycidylester is from 20:80% to 80:20%.

It has been found that the water content in step (d) should be as low as possible to avoid hydrolysis of the diglycidylesters to be formed. Preferably a highly concentrated aqueous solution of alkali metal hydroxide is used in step (d).

For the same reason the hydrolysable chlorine content after step (b) should be minimized (<25000 mg/kg). A too high level can be reduced by known methods such as an increase of the amount of base used or by a reduction of the reaction temperature in step (b).

The following examples and comparative examples are illustrative of the invention, however without restricting its scope to this embodiment.

EXAMPLE 1

A 1 l glass reactor equipped with mechanical stirrer, heating jacket and reflux equipment was charged with 2.76 moles ECH, 3.31 moles of IPA, 2.76 moles of water and 0.345 moles a mixture of 2,2,6,6-tetramethylpimelic acid (70 wt %) and of 2,2,5-trimethyl-5-ethyladipic acid (30 wt %). The mixture was heated to 60° C. and stirred until all of the acid was dissolved. The reaction was started by dosing 0.144 moles of aqueous weight 50% NaOH in 20 minutes, while at the same time increasing the temperature to 84° C. The reaction mixture was kept at this temperature for another 40 minutes and subsequently cooled down to 45° C. in 30 minutes. Then 0.576 moles of aqueous weight 24% NaOH was dosed in 20 minutes and the mixture stirred at 45° C. for another 40 minutes. The stirring was stopped and the mixture settles in two separate phases. The organic phase was flashed off in a rotation film evaporator until the end conditions 100 mbar/110° C. and the residue was subsequently freed from ECH by means of steam distillation (end conditions 120° C./10 mbar). The residue contained about 0.27 wt % hydrolysable chlorine.

This chlorine was reduced by adding 0.82 g (0.01 moles) aqueous weight 50% NaOH to 98.2 g of the residue (=1.3 eq/hydrolysable chlorine) at 45° C. for 60 minutes. Then the resin was diluted to 50 wt % with MIBK, washed three times with 50 ml of water and the MIBK flashed of in a rotation film evaporator until the end conditions 10 mbar/120° C.

The WPE of the final product was 175 eq/g and hydrolysable chlorine content of 440 mg/kg and a total chlorine content of 1100 mg/kg.

EXAMPLE 2

A 1 l glass reactor equipped with mechanical stirrer, heating jacket and reflux equipment was charged with 2.76 moles ECH, 3.31 moles of IPA, 2.76 moles of water and 0.345 moles of mixture of 50 wt % of 2,2,6,6-tetramethylpimelic acid and of 50 wt % of 2,2,5-trimethyl-5-ethyladipic acid. The mixture was heated to 60° C. and stirred until all of the acid was dissolved. The reaction was started by dosing 0.138 moles of aqueous weight 50% NaOH in 20 minutes, while at the same time increasing the temperature to 84° C. The reaction mixture was kept at this temperature for another 40 minutes and subsequently cooled down to 45° C. in 30 minutes. Then 0.5520 moles of aqueous weight 24% NaOH was dosed in 20 minutes and the mixture stirred at 45° C. for another 40 minutes. The stirring was stopped and the mixture settles in two separate phases. The organic phase was flashed off in a rotation film evaporator until the end conditions 100 mbar/110° C. and the residue was subsequently freed from ECH by means of steam distillation (end conditions 120° C./10 mbar). The residue contained about 0.71 wt % hydrolysable chlorine.

This chlorine was reduced by adding 2.01 g (0.025 moles) aqueous weight 50% NaOH to 96.5 g of the residue (=1.3 eq/hydrolysable chlorine) at 45° C. for 60. Then the resin was diluted to 50 wt % with MIBK, washed three times with 50 ml of water and the MIBK flashed of in a rotation film evaporator until the end conditions 10 mbar/120° C.

The WPE of the final product was 175 eq/g and hydrolysable chlorine content of 900 mg/kg and a total chlorine content of 1400 mg/kg.

COMPARATIVE EXAMPLE A

Dodecanediacid was glycidated according to the process described in example 1. The residue after ECH distillation was a white wax, containing no epoxy groups, a hydrolysable chlorine content of 0.78% wt and a little trace of acid (acid value 0.1 meq/kg).

What we claim is:

1. Process for the manufacture of diglycidylesters of α,α,α',α'-branched dicarboxylic acids, comprising:
    (a) the reaction of an α,α,α',α'-branched dicarboxylic acid with a halo substituted monoepoxide, in a 1.1–20 acid equivalent ratio relative to the α,α,α',α'-branched aliphatic dicarboxylic acid, in the presence of a catalyst in an amount of at most 45 mol % of the acid equivalent amount of the α,α,α',α'-branched aliphatic dicarboxylic acid, and at a temperature in the range of from 30 to 110° C., during a period in the range of from 0.5 to 2.5 hr,
    (b) addition of alkali metal hydroxide or alkali metal alkanolate up to an acid equivalent ratio as to the α,α,α',α'-branched aliphatic dicarboxylic acid in the range of from 0.9:1 to 1.2:1, and reaction at a temperature of from 0 to 80° C.,
    (c) distillation of the obtained reaction mixture to remove the excess halo substituted monoepoxide and the solvent and water formed, and
    (d) removal of alkali metal halide salt, in order to complete the dehydrohalogenation.

2. The process of claim 1, wherein the halo substituted monoepoxide comprises an epihalohydrin.

3. The process of claim 1, wherein step (a) is conducted in the presence of water and water-miscible solvent.

4. The process of claim 1, wherein step (a) is conducted in the presence of an aqueous alkanol as solvent.

5. The process of claim 1, wherein the alkali metal halide salt is removed in order to complete the dehydrohalogenation by washing the obtained diglycidylester with water mixed with an inert organic solvent, after treating the residual product with a concentrated aqueous alkali metal hydroxide solution.

6. Process according to claim 1, wherein α,α,α',α'-branched aliphatic dicarboxylic acids, containing from 8 to 24 carbon atoms, are used as starting material.

7. Process according to claim 1, wherein α,α,α',α'-branched aliphatic dicarboxylic acids containing from 8 to 14 carbon atoms in the acid moiety.

8. Process according to claim 7, wherein α,α,α',α'-branched aliphatic dicarboxylic acids of formula I:

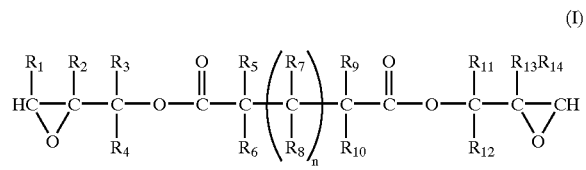

(I)

wherein $R_1, R_2, R_3, R_4, R_5, R_7, R_8, R_9, R_{11}, R_{12}, R_{13}$ and $R_{14}$ may be the same or different and each represent hydrogen or a lower alkyl group containing from 1–4 carbon atoms, wherein $R_6$ and $R_{10}$ may be the same or different and each represent an alkyl group containing from 1 to 10 carbon atoms or a cycloaliphatic ring having 5 or 6 carbon atoms, optionally substituted with one or more lower alkyls, and wherein the total carbon atoms in the diacid part of the diglycidyl esters of formula 1 are in the range of from 8 to 24 carbon atoms, and wherein n is an integer in the range of from 0 to 8.

9. Process according to claim 8, containing from 10 to 14 carbon atoms and wherein n is an integer from 2 to 6, and wherein $R_5$, $R_6$, $R_9$ and $R_{10}$ are methyl or ethyl and $R_7$ and $R_8$ are hydrogen.

10. Process according to claim 1, wherein the reaction time in step (a) is in the range of from 0.9 to 1.5 hours.

11. Process according to claim 1, wherein alkalimetal hydroxides or alkalimetal alkanolates, having from 1 to 6 carbon atoms are used in step (a).

12. Process according to claim 11, wherein sodium hydroxide or potassium hydroxide is used in step (a).

13. Process according to claim 1, wherein aqueous alkanol is used as solvent.

14. Process according to claim 13, wherein the aqueous alkanol solution contains at least one mole alkanol per mol dicarboxylic acid.

15. Process according to claim 1, wherein at most 10 mole % of catalyst, relative to the molar amount of α,α'-branched aliphatic dicarboxylic acid is present in step (a).

16. Process according to claim 1, wherein step (a) is carried out at a temperature in the range of from 65 to 95° C.

17. Process according to claim 1, wherein sodium hydroxide or sodium alkanolate having from 1 to 6 carbon atoms, is used in steps (b) and (d).

18. Process according to claim 17, wherein sodium hydroxide in aqueous solution in a concentration of from 10 to 60 wt % is used in step (b).

19. Process according to claim 18, wherein sodium hydroxide in aqueous solution in a concentration of from 20 to 50 wt % is used.

20. Process according to claim 1, wherein step (b) is carried out at the reaction temperature in the range of from 20 to 70° C.

21. Process according to claims 1, wherein alkalimetal hydroxide or alkalimetal alkanolate is added in step (b) up to an acid equivalent ratio as to the α,α'-branched aliphatic dicarboxylic acid in the range of from 0.95:1 to 1.10:1.

22. Process according to claim 1, wherein highly concentrated sodium hydroxide solutions up to 55 wt % are used in step (d).

* * * * *